United States Patent (10) Patent No.: US 8,999,262 B2
Roehr et al. (45) Date of Patent: Apr. 7, 2015

(54) EXPIRATION INDICATION LABEL

(71) Applicant: Brady Worldwide, Inc., Milwaukee, WI (US)

(72) Inventors: Richard S. Roehr, Hales Corners, WI (US); Matthew M. Kasper, Oak Creek, WI (US); Adam D. Scheuer, Fox Point, WI (US)

(73) Assignee: Brady Worldwide, Inc., Milwaukee, WI (US)

( * ) Notice: Subject to any disclaimer, the term of this patent is extended or adjusted under 35 U.S.C. 154(b) by 256 days.

(21) Appl. No.: 13/833,617

(22) Filed: Mar. 15, 2013

(65) Prior Publication Data

US 2014/0271401 A1 Sep. 18, 2014

(51) Int. Cl.
*G01N 21/75* (2006.01)
*G01N 21/78* (2006.01)
*G04F 1/02* (2006.01)
*G09F 3/00* (2006.01)
*H01B 13/34* (2006.01)
*G04F 1/06* (2006.01)
*H01B 7/36* (2006.01)
*G09F 3/06* (2006.01)
*G01N 33/543* (2006.01)
*G04F 13/00* (2006.01)
*G04F 1/00* (2006.01)
*B41M 5/42* (2006.01)
(Continued)

(52) U.S. Cl.
CPC .............. *G01N 21/78* (2013.01); *H01B 13/344* (2013.01); *G04F 1/06* (2013.01); *H01B 7/368* (2013.01); *G09F 3/06* (2013.01); *G01N 33/54386* (2013.01); *G04F 13/00* (2013.01); *G04F 1/00* (2013.01); *B41M 5/42* (2013.01); *G09F 7/18* (2013.01); *G04F 13/06* (2013.01); *B41M 5/52* (2013.01); *B41M 5/392* (2013.01); *G09F 3/04* (2013.01); *F16L 1/11* (2013.01); *B41M 5/395* (2013.01); *G04F 1/02* (2013.01); *G09F 3/0295* (2013.01); *G09F 3/0291* (2013.01)

(58) Field of Classification Search
CPC .... G01N 21/78; G01N 33/54386; G04F 1/00; G04F 1/06; G04F 13/06; G04F 13/00; B41M 5/392; B41M 5/395; B41M 5/42; B41M 5/52; F16L 1/11; G09F 7/18; G09F 3/04; G09F 3/06; G09F 3/0295; H01B 13/344; H01B 7/368
See application file for complete search history.

(56) References Cited

U.S. PATENT DOCUMENTS

| 4,212,153 A | 7/1980 | Kydonieus et al. |
| 4,539,767 A | 9/1985 | Jaffe |
| 5,092,066 A | 3/1992 | Brewster |
| 5,974,003 A | 10/1999 | Pedicano et al. |
| 7,073,282 B2 | 7/2006 | Savagian et al. |

(Continued)

*Primary Examiner* — Dennis M White
(74) *Attorney, Agent, or Firm* — Whyte Hirschboeck Dudek S.C.

(57) ABSTRACT

A time indicating label for attachment to a tube, the label comprising:
(A) An impermeable facesheet optionally adapted to accepting a graphic before or after attachment of the label to a tube,
(B) An activation layer comprising a polymer matrix and an activating agent, the activation layer in contact with the facesheet,
(C) A release liner impermeable to the activating agent and in contact with the activation layer,
(D) A timing layer comprising a film-forming polymer and a pigment, the timing layer in contact with the release liner,
(E) A dye layer comprising a film-forming polymer and an organic solvent soluble dye and in contact with the timing layer, and
(F) A base layer comprising a material impermeable to the activating agent and dye and in contact with both the dye layer and the activation layer.

12 Claims, 3 Drawing Sheets

(51) Int. Cl.
G09F 7/18 (2006.01)
G04F 13/06 (2006.01)
B41M 5/52 (2006.01)
B41M 5/392 (2006.01)
G09F 3/04 (2006.01)
F16L 1/11 (2006.01)
B41M 5/395 (2006.01)

(56) References Cited

U.S. PATENT DOCUMENTS

| | | |
|---|---|---|
| 7,081,284 B2 | 7/2006 | Hiroishi |
| 7,215,604 B2 | 5/2007 | Haas et al. |
| 2005/0185520 A1 | 8/2005 | Haas et al. |
| 2005/0204594 A1 | 9/2005 | Savagian et al. |
| 2005/0226101 A1 | 10/2005 | Haas et al. |
| 2007/0140068 A1 | 6/2007 | Teffenhart et al. |

EXPIRATION INDICATION LABEL

FIELD OF THE INVENTION

This invention relates to labels. In one aspect the invention relates to labels that indicate the passage of time while in another aspect, the invention relates to labels adapted for attachment to tubing.

BACKGROUND OF THE INVENTION

Time indicating labels are known. For example, U.S. Pat. No. 4,212,153 issued to Kydonieus, et al entitled teaches a time color indicator having a reservoir layer adhesively attached to an indicator layer. In accordance with the Kydonieus patent, a migrating agent in the reservoir layer migrates through the adhesive layer and the indicator layer to the top or front surface of the indicator layer. The Kydonieus patent also teaches that the reservoir layer is preferably mounted on a barrier layer with an adhesive and release sheet on top of the reservoir layer. The indicator is activated by removing the release sheet and applying an indicator layer to the adhesive layer.

Kydonieus further teaches that the indicator layer is a solid sheet or film of non-porous polymer which allows migration of the chosen agent, and that appropriate indicator layer materials include plasticized PVC, semi-plasticized PVC, rigid PVC, acrylics, polyurethanes and thermoplastic polyester elastomers. The Kydonieus indicator layer is 2 to 14 mils thick. The reservoir layer is preferably made from a plastisol, although vinyl chloride/vinyl acetate copolymer, a urethane polymer, a polyolefin, a thermoplastic polyester elastomer, and polyvinyl chloride may be used in forming the reservoir layer. Kydonieus teaches that the reservoir layer should be 1 to 20 mils thick, and is preferably 1 to 5 mils thick. One suggested application for the Kydonieus device is greeting cards Variations on the Kydonieus device are taught in U.S. Pat. Nos. 5,974,003 and 7,215,604. However, none of these labels are adapted for attachment to tubing, e.g., tubing associated with intravenous (IV) bags, and similar structures. Disclosures that do teach methods for attaching a label to a wire or tube include U.S. Pat. Nos. 4,539,767, 5,092,066 and 7,073,282 but these methods of attachment do not allow for easy re-positioning of the label after attachment to the wire or tube.

Of continuing interest is a time indicating, or expiration indication, label that attaches easily to a tube, is easily re-positioned on the tube after attachment, can carry a graphic which can be applied before and/or after attachment to the tube, and provides a reliable and easily discernible indication of a pre-determined elapse of time.

SUMMARY OF THE INVENTION

In one embodiment the invention is a time indicating label for attachment to a tube, the label comprising:
  (A) An impermeable facesheet having first and second facial surfaces, the first facial surface adapted to accepting a graphic before or after attachment of the label to a tube,
  (B) An activation layer comprising a polymer matrix and an activating agent, the activation layer having first and second facial surfaces, the first facial surface of the activation layer in contact with the second facial surface of the facesheet,
  (C) A barrier tape impermeable to the activating agent of the activation layer, the barrier tape having first and second facial surfaces, the first facial surface of the barrier tape in partial contact with the activation layer,
  (D) An impermeable release liner having first and second facial surfaces, the first facial surface of the release liner in contact with that part of the second facial surface of the activation layer not in contact with the first facial surface of the barrier tape,
  (E) A timing layer comprising a film-forming polymer resin and a pigment, the timing layer having first and second facial surfaces, the first facial surface of the timing layer in contact with the second facial surface of the barrier tape and the second facial surface of the release liner,
  (F) A dye layer comprising a film-forming polymer resin and an organic dye soluble in the activating agent, the dye layer having first and second facial surfaces, the first facial surface of the dye layer in contact with the second facial surface of the timing layer, and
  (G) A base layer comprising a substrate impermeable to the dye of the dye layer and the activating agent of the activation layer, the base layer having first and second facial surfaces, the first facial surface of the base layer in contact with the second facial surface of the dye layer;
with the provisos that the:
  (1) Part of the base layer extending beyond the barrier tape and activating layer comprises at least one aperture sized to accept a tube of a pre-determined diameter,
  (2) Release liner can be removed from the activation layer with less than 20 grams per inch width (g/in width) of force,
  (3) Release liner film has stiffness as measured by Taber stiffness greater than the facesheet; and
  (4) The timing layer, the dye layer and base layer comprise a bottom sheet component of the label, the bottom sheet having a Taber stiffness of greater than 0.1.

In one embodiment the invention is a time indicating label for attachment to a tube, the label comprising:
  (A) An impermeable facesheet having first and second facial surfaces, the first facial surface adapted to accepting a graphic before or after attachment of the label to a tube,
  (B) An activation layer comprising a polymer matrix and an activating agent, the activation layer having first and second facial surfaces, the first facial surface of the activation layer in contact with the second facial surface of the facesheet,
  (C) A release liner impermeable to the activating agent of the activation layer, the release liner having first and second facial surfaces, the first facial surface of the release liner in partial contact with the second facial surface of the activation layer,
  (D) A timing layer comprising a film-forming polymer resin and a pigment, the timing layer having first and second facial surfaces, the first facial surface of the timing layer in contact with the second facial surface of the release liner,
  (E) A dye layer comprising a film-forming polymer resin and an organic dye soluble in the activating agent, the dye layer having first and second facial surfaces, the first facial surface of the dye layer in contact with the second facial surface of the timing layer, and
  (F) A base layer comprising a substrate impermeable to the dye of the dye layer and activating agent of the activation layer, the base layer having first and second facial surfaces, the first facial surface of the base layer in contact with both the second facial surface of the dye layer and that part of the activation layer not in contact with the release liner, with the provisos that the:
(1) Part of the label in which the base layer is in contact with the activation layer comprises at least one aperture sized to accept a tube of a pre-determined diameter,
(2) Release liner can be removed from the activation layer with less than 20 grams per inch width (g/in width) of force,
(3) Release liner film has stiffness as measured by Taber stiffness greater than the facesheet; and
(4) Combination of the timing layer in contact with the dye layer which is also in contact with the base layer constitute a bottom sheet component of the label with a Taber stiffness of greater than 0.1.

In one embodiment the invention is the label described in one of the previous embodiments in activated form, i.e., with the release liner removed and the second facial surface of the activation layer in contact with the first facial surface of the bottom sheet.

In one embodiment the invention is a carrier strip comprising a plurality of one embodiment of the non-activated labels of this invention. In one embodiment the invention is the label, either in non-activated or activated form, attached to a tube. In one embodiment the label is attached to an IV tube.

DETAILED DESCRIPTION OF THE PREFERRED EMBODIMENT

Definitions

Figure 1A:
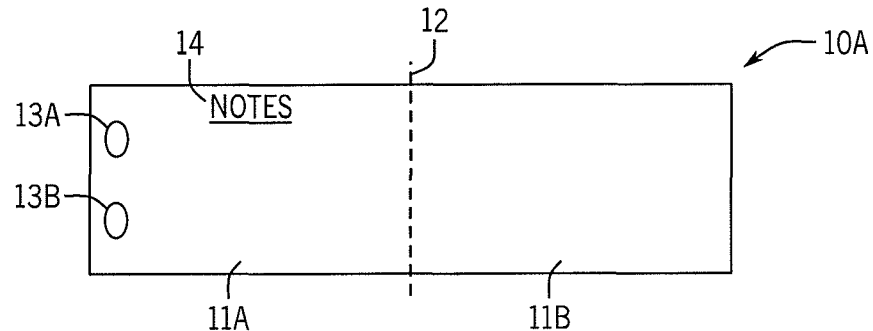
FIG. 1A is a top plan view of a schematic of a pre-activated label of this invention.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, temperature, is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the force necessary to remove the release liner from the adhesive, and the stiffness of the label.

"Comprising", "including", "having" and like terms mean that the composition, process, etc. is not limited to the components, steps, etc. disclosed, but rather can include other, undisclosed components, steps, etc. In contrast, the term "consisting essentially of" excludes from the scope of any composition, process, etc. any other component, step etc. excepting those that are not essential to the performance, operability or the like of the composition, process, etc. The term "consisting of" excludes from a composition, process, etc., any component, step, etc. not specifically disclosed. The term "or", unless stated otherwise, refers to the disclosed members individually as well as in any combination.

"Facial surface", "planar surface", "top surface", "bottom surface" and the like are used in distinction to "edge surface". If rectangular in shape or configuration, a label will comprise two opposing facial surfaces joined by four edge surfaces (two opposing pairs of edge surfaces, each pair intersecting the other pair at right angles). If circular in configuration, then the label will comprise two opposing facial surfaces joined by one continuous edge surface.

"Ink" and like terms mean a coatable or printable formulation that can and usually does contain a dye and/or pigment.

"Dye" and like terms mean a visible light absorbing compound that is present in a molecularly dispersed (dissolved) form.

"Pigment" and like terms mean a visible light absorbing material or compound that is present in a non-molecularly dispersed (particulate) form.

"Graphic", "graphic image" and like terms mean text or pictorial representations formed of ink or other dye or pigment substances. Graphics include, but are not limited to, words, numbers, bar codes, pictures, designs (geometric or otherwise), and solid colors (typically applied by flood coating).

"Layer" means a single thickness, coating or stratum spread out or covering a surface.

"Multi-layer" means two or more layers with adjacent layers in contact with each other.

"Impermeable" and like terms mean a layer, e.g., a film, coating, etc., that effectively prevents passage of the activating compound from one layer to another layer, or from one layer to an exterior facial surface of an exterior layer of the label.

"Tube" includes tubing, wires, conduit, cable, hoses, and the like.

"Taber stiffness" and like terms mean the stiffness of a material as measured by a Taber Stiffness Tester, e.g., Taber V-5 model 150E or model 150B, available from Taber Industries, and expressed in Taber stiffness units.

Facesheet

The facesheet can be transparent or translucent but not opaque, and its chemical composition is not critical to the invention so long as it has sufficient film integrity for its intended use. Typically, it comprises impermeable polyester, such as a condensation product of terephthalic acid and a glycol, e.g., ethylene glycol, isophthalic acid and a glycol, or mixtures of terephthalic acid, isophthalic acid and a glycol, or a polyetherimide. One particularly useful family of films of this type is a highly oriented polyester film known in the trade as MELINEX®, which can be print treated or non-print treated. Other useful films can be constructed from polyethylene naphthalate (PEN) or polyetherimide (PEI).

Still other useful polymeric films include impermeable films of acrylic polymers and interpolymers; cellulosic polymers, including cellulose acetate, cellulose acetate butyrate, cellulose acetate propionate and mixtures of these polymers; polyolefins, including homopolymers and interpolymers of ethylene or propylene; polyethersulfone (PES); polysulfone; and other polymeric films which are flexible and sufficiently strong to be used as label facestocks. The polymeric film typically has a thickness of 1 or more mils, preferably of 1 to 2 mils.

In one embodiment the top, i.e., the first, facial surface of the facesheet is treated or coated to facilitate receiving and holding an ink, dye and/or pigment in the form of a graphic. The graphic can be applied before and/or after it is attached to a tube. The graphic can be applied in any manner, e.g., any form of printing, handwriting with a pencil, pen or marker, etc.

The treatment of the first facial surface of the facesheet can be in any manner that facilitates the reception and/or holding of the graphic media, e.g., mechanical abrasion, corona or flame treatment, acid wash, etc., or a coating can be applied. Suitable topcoats are described in U.S. Pat. No. 7,081,284. The thickness of the topcoat typically ranges from 0.3 to 2.5 mils, preferably from 0.3 to 1 mil. The topcoat can be applied in any manner, e.g., slot die, rod, roll coating (reverse roll, gravure roll, roll blade, flexographic, etc.), dip bath, spraying and the like.

Activation Layer

The activating layer, also known as the activation or enhancement layer, is typically colorless and comprises a plasticizer and a polymer resin. The plasticizer, also known as a migrating agent, is compatible, i.e., soluble, with the dye of the dye layer and the resin of the timing layer. Monomeric and polymeric plasticizers can be used, and these plasticizers include but are not limited to PLASTHALL® P-550 (a polyester glutarate), PLASTHALL® 7050 (a dialkyl diether glutarate), PLASTHALL® TOTM (trioctyl trimellitate), and PARAPLEX® G-25 (a polyester sebacate), all available from The HallStar Company.

Any film-forming polymer resin that can be solubilized by the plasticizer can be used in the activating layer, and representative polymer resins include, but are not limited to, polyurethane, polyester, natural or synthetic rubber, rubber-acrylic hybrid, polyamide, polyethylene-vinyl acetate, acrylic, and the like, with polyurethane resins preferred. The weight average molecular weight (Mw) of the resin can vary widely, but it is typically between 5,000 and 1,000,000, more typically between 10,000 and 40,000, grams per mole.

The plasticizer is admixed with the resin to facilitate ease of activation and storage stability of the plasticizer. Typically, the activating layer comprises 5 to 60, more typically 15 to 40, weight percent (wt %) of the plasticizer. In a preferred embodiment, utilizing a non-pressure sensitive polymer resin, such as ESTANE 5703 from Lubrizol, allows for the incorporation of higher loadings of plasticizer to enhance the migration of the dye. Typically, the remainder of the layer comprises the polymer resin although the layer can comprise other components as well, e.g., antioxidants, UV-inhibitors, etc., but these other components are typically used in nominal amounts, e.g., less than 2, more typically less than 1, wt % of the activating layer. Tackifying agents known to the art can be added to increase adhesion to the timing layer surface. Typically, the amount of tackifying agent ranges from 1 to 30 parts based on total solids.

The thickness of the activating layer is, like the thickness of the topsheet, a function of a number of different variables including but not limited to the desired timing, design thickness of the indicator, the nature and amount of plasticizer, the nature of the polymer resin, cost and the like, but typically the thickness is from 0.2 to 3 mil (0.00508 to 0.0762 mm), more typically from 0.5 to 1.5 mil (0.0127 to 0.0381 mm). The activating layer comprises first and second facial surfaces with the first facial surface in contact with the second facial surface of the topsheet and the second facial surface, depending upon the state of the time indicator, covered with a release liner (when the label is in an inactive state), open to the environment (during the act of activation, i.e., upon removal of the release liner), or in contact with a facial surface of the timing layer (when the label is in an active state, i.e., when the activating layer has been brought in contact with the timing layer of the bottom sheet).

Release Liner

The construction of the release liner is not particularly important to the practice of this invention other than to be impermeable to the activating agent, i.e., to serve as a block to the activating agent migrating into and activating the timing agent and dye. Examples of materials that can be used for the liner include glassine paper, laminated paper, polyester film and polyolefin, e.g., polypropylene, film, preferably comprising a coating of silicone. The liner can also serve as an activation indicator if it is opaque. When the liner is removed during activation, the bottom layer becomes visible serving as a means to indicate that the timer is in use.

The release liner is positioned between the activation layer and the bottom sheet or timing layer such that it covers the activation layer, typically the half of the facesheet distal from the apertures in the label. The release liner can extend beyond the activation layer of the second facial surface of the facesheet, but this is usually avoided since it serves no useful purpose. However, the release liner can extend outside of the edges of the facesheet so as to provide a finger grip to ease its removal from the label at the time activation of the timing and dye component is desired.

One of the hallmarks of this invention is the ease of removal of the release liner from the activation layer. The adhesive of the activation layer and the composition of the release liner are chosen so as to provide peel strength of less than 20, preferably less than 10 and more preferably less than 5 g/in width as measured by Pressure Sensitive Tape Council (PSTC-4). A peel force of this magnitude combined with the appropriate stiffness of the release liner allows for the easy activation of the expiration indicating label in settings in which the hands manipulating the label are gloved, e.g., a hospital setting in which latex or nitrile gloves are typically worn. Appropriate stiffness for the release liner is typically 0.1 to 0.5 Taber units and is greater than the facesheet stiffness.

Barrier Tape

The barrier tape, also known as a protective tape, is impermeable to the activating agent, i.e., it serves as a block to the activating agent migrating into and activating the timing agent and dye. The barrier tape construction contains a backing with a pressure sensitive adhesive. Examples of materials that can be used for the barrier tape include various papers, laminated paper, polyester film and polyolefin, e.g., polypropylene, film, preferably comprising a coating of pressure sensitive adhesive. The barrier tape can be transparent or opaque. The barrier tape is positioned and laminated between the activation layer and the bottom sheet or timing layer such that it covers that part of the activation layer not covered by the release liner.

Bottom Sheet

The bottom sheet of the label is multilayered and comprises the timing layer, dye layer and base layer. The first facial surface of the bottom sheet and the first facial surface of the timing layer are one and the same, and the second facial surface of the bottom sheet and the second facial surface of the base layer are also one and the same.

Timing Layer

The timing layer comprises a polymer resin and a pigment. Like the activating layer, any film-forming polymer resin can be used for the timing layer, and representative polymer resins include, but are not limited to, acrylic, polyurethane, polyester and the like, with polyurethane and polyester resins preferred. The weight average molecular weight (Mw) of the resin can vary widely, and it is typically between 5,000 and 1,000,000, more typically between 10,000 and 40,000, grams per mole.

The pigment can be any reflective, opaque, or absorptive substance such as aluminum, stainless steel, natural and synthetic mica, coated glasses, metal oxides, silicates, bismuth oxychloride, calcium carbonate, barium sulfate, carbon black but is typically and preferably aluminum flake and/or titanium dioxide ($TiO_2$). Aluminum flake is a preferred pigment because its high reflectivity and opacity reduces the visibility of the dye as it migrates through the timing layer, minimizing the grey time or, in other words, the time that exists between the start of color development to the completion of the color development (both as observed by a machine or the unaided eye). For example, a preferred, film-forming timing layer that is constructed using equal parts of either $TiO_2$ or aluminum flake has an opacity of 82% and 100%, respectively, per ASTM D2805. The $TiO_2$ containing construction will appear pink prior to activation due to low opacity while the aluminum flake containing construction will have no pink color. In one embodiment, the typical amount of pigment in the dried coating is in the range of 15 to 65 wt % based on the weight of the coating.

The thickness of the timing layer is, like the thickness of the topsheet and activating layer, a function of a number of different variables including but not limited to the desired timing, design thickness of the time indicator, the nature and amount of pigment, the nature of the polymer resin, cost and the like, but typically the thickness is from 0.2 to 3 mil (0.00508 to 0.0762 mm), more typically from 0.5 to 1.5 mil (0.0127 to 0.0381 mm). The timing layer comprises first and second facial surfaces with the first facial surface, depending upon the state of the time indicator, covered with a protective or release layer, open to the environment, or in contact with the facial surface of the activating layer. The second facial surface of the timing layer is in contact with the first facial surface of the dye layer. The first facial surface of the timing layer is the first facial surface of the bottom sheet or, in other words, the first facial surface of the timing layer and the first facial surface of the bottom sheet are one and the same.

The timing layer can comprise indicia, e.g., a preprinted graphic such as the word "EXPIRED" or "VOID", that is visible by machine or to the naked eye under typical viewing conditions only after the timing layer has expired. If a graphic is present, then it is printed on the first facial surface of the timing layer and as such, the second facial surface of the graphic is in contact with the first facial surface of the timing layer, and the first facial surface of the graphic is in contact with the second facial surface of the release liner. Upon removal of the release liner, it is in contact with the second facial surface of the activating layer.

Dye Layer

The dye layer comprises a polymer resin and dye soluble in the activating agent. Like the activating and timing layers, any film-forming polymer resin can be used for the dye layer, and representative polymer resins include, but are not limited to, acrylic, polyurethane, polyester, polyvinyl chloride, rubber, rubber-acrylic hybrid and the like, with polyurethane and polyester resins preferred. The weight average molecular weight (Mw) of the resin can vary widely, and it is typically between 5,000 and 1,000,000, more typically between 10,000 and 40,000, grams per mole.

The dye of the dye layer is water-insoluble but soluble in either or both nonpolar and polar organic solvents such as such as various aromatic and aliphatic hydrocarbons like toluene, xylene, pentane, etc., and various ketones, acetates, ethers, esters, alcohols, etc. The dye is also soluble in the resin and plasticizer of the activating layer. A wide variety of dyes, typically and preferably organic dyes, can be used in the practice of this invention including diazo dyes, carbonyl dyes, polymethine dyes, azomethine dyes, triarylmethane dyes, indoaniline dyes, indophenol dyes, xanthine dyes, oxazine dyes, and thiazine dyes although the dyes of the anthraquinone, methine and azo dye families are preferred. The dyes are typically used at a concentration of 1-30 parts, preferably 10-25 parts solids in the dye layer. The thickness of the dye layer is, like the thickness of the topsheet, activating and timing layers, a function of a number of different variables including but not limited to the design thickness of the time indicator, the nature and amount of pigment, the nature of the polymer resin, cost and the like, but typically the thickness is from 0.001 to 1 mil (0.0000254 to 0.0254 mm), more typically from 0.05 to 0.2 mil (0.00127 to 0.00508 mm). Solubilizing the dye in an organic solvent makes it more uniformly available to the solubilizing action of the plasticizer than if it was in a particulate or dispersed form, such as solvent soluble dye particulates dispersed in water-based coating.

The dye layer can comprise indicia, e.g., a preprinted graphic such as the word "EXPIRED" or "VOID", that is visible by machine or to the naked eye under typical viewing conditions only after the timing layer has expired. If a graphic is present, then it is printed on the first facial surface of the dye layer and as such, the second facial surface of the graphic is in contact with the first facial surface of the dye layer, and the first facial surface of the graphic is in contact with the second facial surface of the timing layer.

Base Layer

The base layer of the bottom sheet can be any substrate, typically a film or paper, whose structural integrity is not compromised or otherwise affected by the plasticizer and/or dye. The substrate is such that neither the plasticizer nor dye will bleed into its second facial surface, i.e., one of the external surfaces of the label, under normal storage and use conditions, e.g., room temperature, pressure and humidity. Exemplary substrate layers include, but are not limited to, various polymeric films such as polyesters, polyimides, polyolefins, polycarbonates, various nonpolymeric materials such as glassine or wax paper, woven and non-woven papers or fabrics, and metal foils. In one embodiment, the preferred substrate is an organic solvent, plasticizer and dye impermeable polymeric film that will provide a uniform, smooth surface for the dye and timing layers which, in turn, will improve the consistency and accuracy of dye migration after activation.

In one embodiment all of the edge surfaces of the base layer are co-terminus with all of the corresponding edge surfaces of the dye and timing layers. In this embodiment the bottom sheet component of the label extends beyond the top component of the label, i.e., the combination of the facesheet, activation layer and optional barrier tape, and the apertures by which the label is attached to a tube are located in this extension area.

In one embodiment the base layer extends beyond one of the co-terminus edges of the dye and timing layers and beyond the co-terminus edges of the top component of the label. In this embodiment the extension area of the bottom sheet also comprises the apertures.

Assembly of the Label

Dye and Timing Layer Construction

The dye layer needs to adhere to the base substrate, and it is typically applied to the base substrate using a printing or coating technique, e.g., flexographic, gravure, screen, Meyer rod or the like. Typically, the polymer resin chemistry of the timing and dye layers is compatible which provides good adhesion and minimizes the interface between the two layers through which the plasticizer needs to migrate. The timing layer can be applied to the dye layer in any convenient manner but is typically applied by means of heat lamination and without the use of an adhesive. If heat lamination is chosen as the method for applying the dye layer, proper selection of processing controls such as lamination temperature, roller speed and pressure are necessary to control and minimize the migration of the dye into the timing layer, and this selection is well within the knowledge of those skilled in the art. Similar to the activating layer, the timing layer can be protected by an optional release liner until it is ready to be joined to the activating layer. In certain constructions of the label, a common release liner separates the activating and timing layers.

Total Label Construction

In one embodiment, a preferred embodiment, the label of this invention is constructed by first printing the bottom sheet, either the first facial surface of the timing layer or dye layer, with desired indicia followed by affixing an optional protective tape to prevent migration of the activating agent into the bottom sheet. The activation layer with release liner is back-scored to slit the liner to appropriate width, while the outside edge segment of release liner is removed as the activating layer is laminated to the bottom sheet. The edges are then trimmed off the bottom sheet followed by creation of the desired aperture(s). The preferred number of apertures ranges from 1 to 3. The activation layer is then die cut to the appropriate dimension and perforated between individual labels. For ease of use in high volume manufacturing, the labels are packaged in roll form. Individual labels are removed from the roll and applied to a tube. When ready for use, the release liner is removed and the two sections of the label that were separated by the common release liner, are joined together, typically by pressing the open surface of the activating layer against the open surface of the timing layer to form an activated time indicator.

One of the hallmarks of this invention is the stiffness of that end of the label proximal to the apertures. The stiffness of the proximal end of the label with the apertures is expressed in terms of its Taber stiffness as measured by ASTM D747 and has a stiffness from 0.1 to 6.0, typically from 0.1 to 1.0 and more typically from 0.1 to 0.5, Taber units. A label stiffness in these ranges allows for ease of attachment, holding position and repositioning on tubing, wires, conduit, cable, hoses, and the like.

Specific Embodiments

Figure 2A:
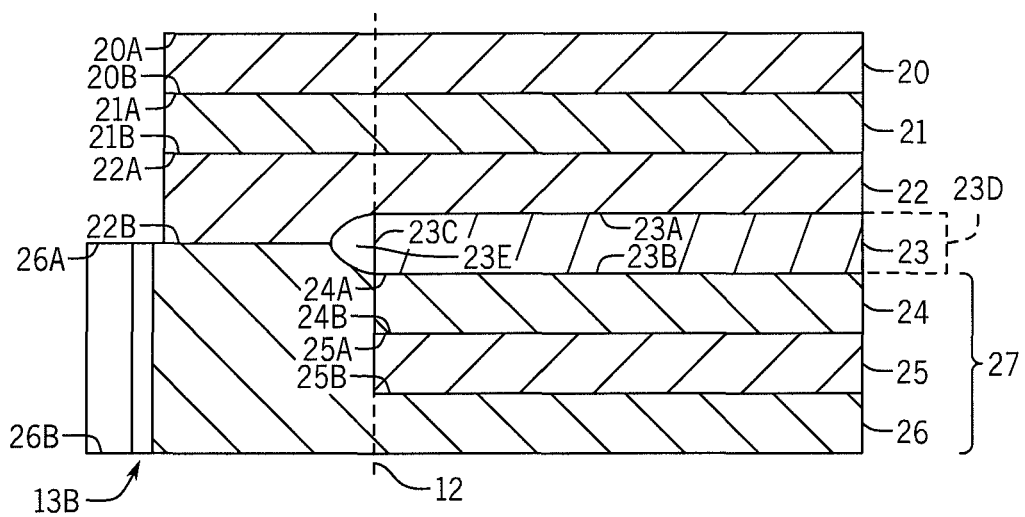
FIG. 2A is cross-sectional view of FIG. 1A taken along line 2A-2A.

FIG. 1A is a top plan view of a schematic of a pre-activated label of this invention. Pre-activated label 10A is divided into two sections by line 12-12. The placement of line 12-12 along the length of label 10A can vary although it typically is located at or near, e.g., within 10 percent in either direction, of the midpoint. Line 12-12 represents the extent to which release sheet 23 (FIG. 2A) is in contact with activation layer 22 and bottom sheet 27 (FIG. 2A). Notes section 11A comprises elliptical apertures 13A and 13B and graphic "Notes" 14. Time-indicating section 11B is distal from apertures 13A and 13B.

Figure 1B:
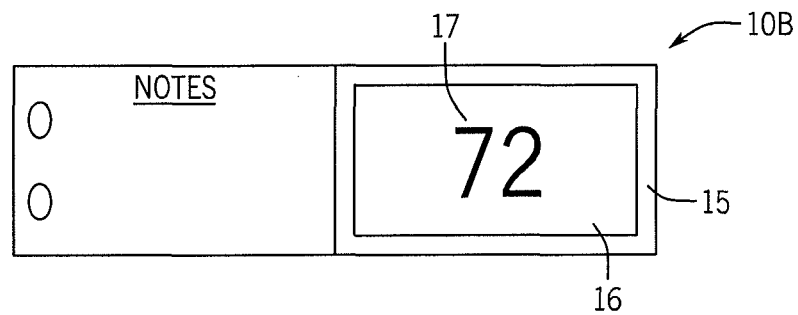
FIG. 1B is a top plan view of a schematic of a post-activated label of this invention.

FIG. 1B shows FIG. 1A post-activation. Time-indicating section 11B of post-activation label 10B has visibly exposed border 15 designed as a reference color frame to aid in determining the desired indication end point. Graphic 17 is selected to indicate the expiration period for the label design. Here depicted is a number (72) indicating the number of hours that will have passed from when the label was activated until the indication area 16 matches the reference frame color 15. In one embodiment not shown, reference frame color 15 is printed or otherwise applied to time indicating section 11B prior to activation of the label. In the embodiment of FIG. 1B, reference frame color appears after activation of the label.

FIG. 2A is a schematic cross-section of the pre-activated label of FIG. 1A taken along line 2A-2A. Optional topcoat 20 is typically provided to enhance the ink receptivity and retention of facesheet 21, and second facial surface 20B is in contact with first facial surface 21A of facesheet 21. First facial surface 20A of optional topcoat 20 is open to the environment.

Second facial surface 21B of facesheet 21 is in contact with first facial surface 22A of activation layer 22. Second facial surface 22B of activation layer 22 is in contact with both first facial surface 26A of base layer 26 and first facial surface 23A of release sheet 23. Edge surface 23C is the extent to which release sheet 23 extends into label 10A, and this extent is represented by line 12-12 which, as noted above, divides label 10A into notes section 11A and time-indicating section 11B. Since edge surface 23C usually does not provide a full contact surface for second facial surface 22B and first facial surface 26A, typically small gap 23E exists between these three surfaces. Release sheet 23 optionally extends beyond the edge of label 10A (as defined by the co-terminus edges of layers 20-22 and 24-26) to form finger-grip 23D.

Bottom sheet 27 comprises timing layer 24, dye layer 25 and base layer 26. In this embodiment first facial surface 24A of timing layer 24 is also the first facial surface of bottom sheet 27, and second facial surface 26B of base layer 26 is also the second facial surface of bottom sheet 27.

Second facial surface 24B of timing layer 24 is in contact with first facial surface 25A of dye layer 25, and second facial surface 25B of dye layer 25 is in contact with first facial surface 26A of base layer 26. Second facial surface 26B of bottom film 26 is open to the environment.

Figure 2B:
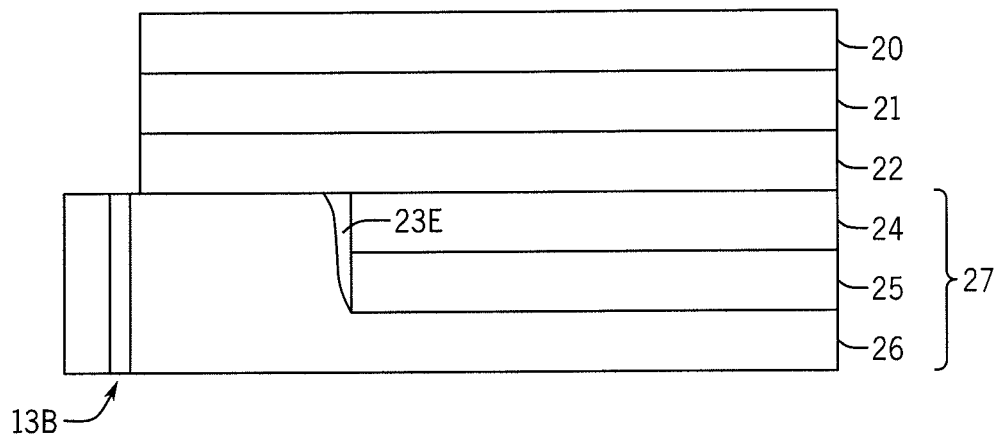
FIG. 2B is cross-sectional view of FIG. 1B taken along line 2B-2B.

FIG. 2B illustrates the label of FIG. 2A after activation, i.e., after release liner 23 is removed from label 10A and activation layer 22 is pressed into contact with timing layer 24. Gap 23E is now shifted deeper into the label construction and minimally enlarged to accommodate the removal of release liner 23.

Figure 2C:
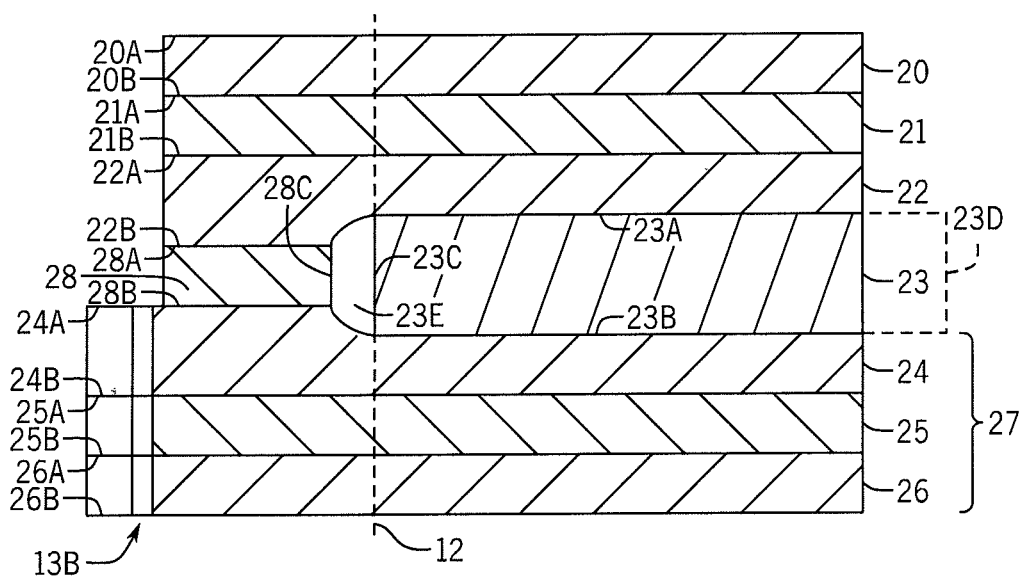
FIG. 2C is cross-sectional view of FIG. 1A taken along line 2A-2A and comprising an optional barrier tape.

FIG. 2C illustrates another embodiment of the label of this invention. In this embodiment protective tape 28 is positioned within the label such that first facial surface 28A is in partial contact with second facial surface 22b and second facial surface 28B is in partial contact with first facial surface 24A. Ideally, edge surface 28C is in contact with edge surface 23C but if abutment is not possible for whatever reason, then these two edge surfaces are as close to one another as possible. In one embodiment one of edge surfaces 28C and 23C overlaps the other edge. Protective tape 28, in combination with release liner 23, prevents the bleed of activating agent from activation layer 22 into timing layer 24.

Figure 2D:
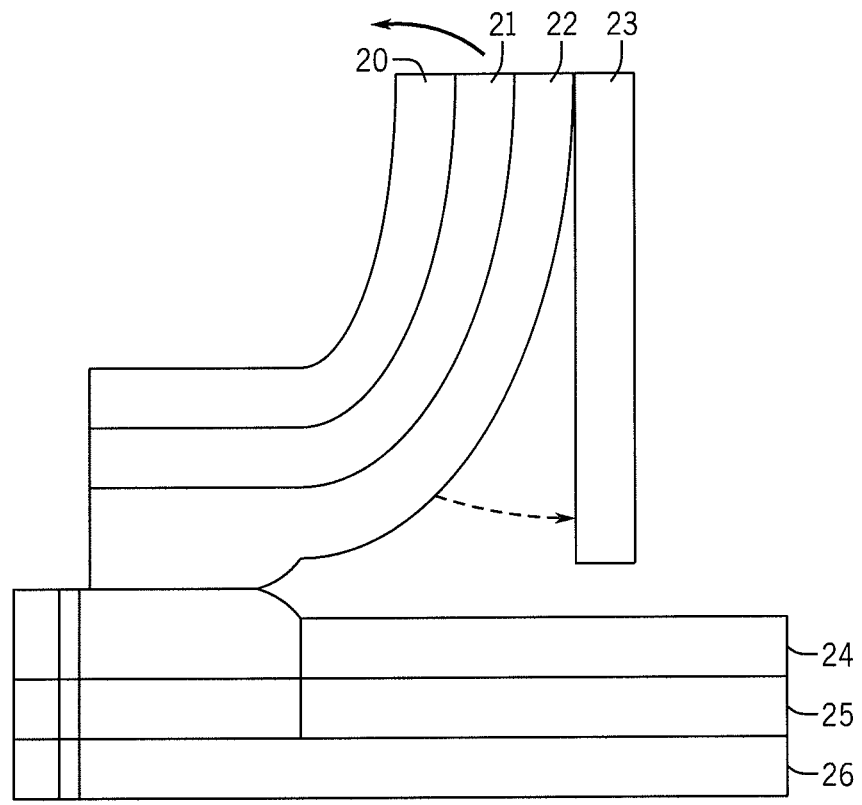
FIG. 2D is cross-sectional view of FIG. 1A taken along line 2A-2A during the activation step.

FIG. 2D illustrates the method for activating the label. To activate label 10A, a user simply lifts the top component of the label, i.e., the composite of 20, 21, 22 and 23, and then bends from the distal end to the proximal end. This action coupled with the differential stiffness of release liner 23 and coated composite 20, 21 and 22 and the release force results in release liner 23 lifting away from activation layer 22 starting at line 12. The coated composite 20, 21 and 22 is laminated to timing layer 24 while removing liner 23 and applying finger pressure from the proximal to distal end of label. The activating agent within activation layer 22 will then migrate over time into and through timing layer 24 and into dye layer 25 in which it will solubilize the dye. The dye will subsequently migrate through timing layer 24 and into activation layer 22. When the color intensity of the dye in indication area 16 matches the reference color frame 15, the expiration period is reached.

Figure 3:
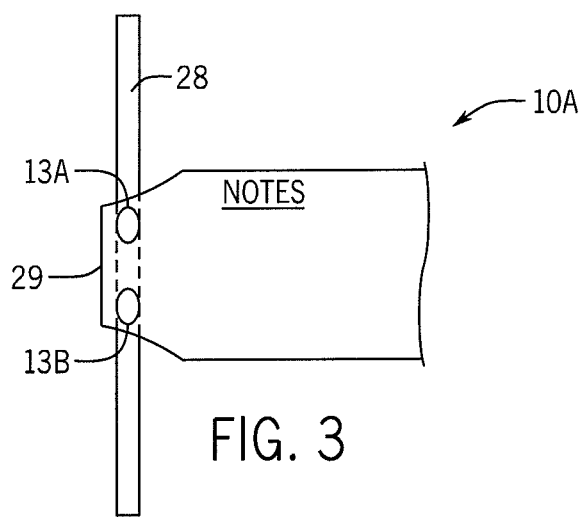
FIG. 3 is a top plan view of the label of either FIG. 1A or 1B attached to a tube.

FIG. 3 is a schematic top view of label 10A attached to tube 28. As shown in this figure, in one embodiment the Notes section of label 10A is pinched in such a manner so that tube 28 can pass through aperture 13B, under section 29 of the label between apertures 13A and 13B, and through aperture 13A. Once tube 28 has passed through these two apertures, the pinch of label 10A is released and label 10A expands to near its normal width except that the friction contact between tube 28 and the edges of the two apertures is such so that label 10A is retained in position on tube 28. If re-positioning of the label is desired, the label is simply pinched to overcome the static friction contact, the label or tube slid to the desired new location, and the pinch then released to re-establish static friction between the tube and edges of the apertures.

In another embodiment not shown, tube 28 can pass through the two apertures but over section 29 of label 10A, i.e., the tube now passes under the label before entering aperture 13B and after exiting aperture 13A. In another embodiment, not shown, the label is equipped with three or more apertures positioned in a straight line. In yet another embodiment not shown, slits can extend from an edge surface of the Notes section of the label to each aperture thus eliminating the need to thread tube 28 through the two apertures and over or under section 29. This embodiment is particularly useful in those situations in which the label is to be attached to a tube or rod without a free or open end.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

We claim:

1. A time indicating label for attachment to a tube, the label comprising:
   (A) An impermeable facesheet having first and second facial surfaces, the first facial surface adapted to accepting a graphic before or after attachment of the label to a tube,
   (B) An activation layer comprising a polymer matrix and an activating agent, the activation layer having first and second facial surfaces, the first facial surface of the activation layer in contact with the second facial surface of the facesheet,
   (C) A barrier tape impermeable to the activating agent of the activation layer, the barrier tape having first and second facial surfaces, the first facial surface of the barrier tape in partial contact with the activation layer,
   (D) An impermeable release liner having first and second facial surfaces, the first facial surface of the release liner in contact with that part of the second facial surface of the activation layer not in contact with the first facial surface of the barrier tape,
   (E) A timing layer comprising a film-forming polymer resin and a pigment, the timing layer having first and second facial surfaces, the first facial surface of the timing layer in contact with the second facial surface of the barrier tape and the second facial surface of the release liner,
   (F) A dye layer comprising a film-forming polymer resin and an organic dye soluble in the activating agent, the dye layer having first and second facial surfaces, the first facial surface of the dye layer in contact with the second facial surface of the timing layer, and
   (G) A base layer comprising a substrate impermeable to the dye of the dye layer and the activating agent of the activation layer, the base layer having first and second facial surfaces, the first facial surface of the base layer in contact with the second facial surface of the dye layer;
   with the provisos that the:
   (1) Part of the base layer extending beyond the barrier tape and activating layer comprises at least one aperture sized to accept a tube of a pre-determined diameter,
   (2) Release liner can be removed from the activation layer with less than 20 grams per inch width (g/in width) of force,
   (3) Release liner film has stiffness as measured by Taber stiffness greater than the facesheet; and
   (4) The timing layer, the dye layer and base layer comprise a bottom sheet component of the label, the bottom sheet having a Taber stiffness of greater than 0.1.

2. The label of claim 1 further comprising a reference color frame.

3. The label of claim 1 in which the at least one aperture is elliptical in shape.

4. The label of claim 1 attached to a carrier strip.

5. The label of claim 1 attached to a tube.

6. The label of claim 5 in which the tube is an IV tube.

7. A time indicating label for attachment to a tube, the label comprising:
   (A) An impermeable facesheet having first and second facial surfaces, the first facial surface adapted to accepting a graphic before or after attachment of the label to a tube,
   (B) An activation layer comprising a polymer matrix and an activating agent, the activation layer having first and second facial surfaces, the first facial surface of the activation layer in contact with the second facial surface of the facesheet, (C) A release liner impermeable to the activating agent of the activation layer, the release liner having first and second facial surfaces, the first facial surface of the release liner in partial contact with the second facial surface of the activation layer, (D) A timing layer comprising a film-forming polymer resin and a pigment, the timing layer having first and second facial surfaces, the first facial surface of the timing layer in contact with the second facial surface of the release liner, (E) A dye layer comprising a film-forming polymer resin and an organic dye soluble in the activating agent, the dye layer having first and second facial surfaces, the first facial surface of the dye layer in contact with the second facial surface of the timing layer, and (F) A base layer comprising a substrate impermeable to the dye of the dye layer and activating agent of the activation layer, the base layer having first and second facial surfaces, the first facial surface of the base layer in contact with both the second facial surface of the dye layer and that part of the activation layer not in contact with the release liner, with the provisos that the:

(1) Part of the label in which the base layer is in contact with the activation layer comprises at least one aperture sized to accept a tube of a pre-determined diameter, (2) Release liner can be removed from the activation layer with less than 20 grams per inch width (g/in width) of force, (3) Release liner film has stiffness as measured by Taber stiffness greater than the facesheet; and (4) Combination of the timing layer in contact with the dye layer which is also in contact with the base layer constitutes a bottom sheet component of the label with a Taber stiffness of greater than 0.1.

8. The label of claim 7 further comprising a reference color frame.

9. The label of claim 7 in which the at least one aperture is elliptical in shape.

10. The label of claim 7 attached to a carrier strip.

11. The label of claim 7 attached to a tube.

12. The label of claim 11 in which the tube is an IV tube.

\* \* \* \* \*